United States Patent [19]

Gordon

[11] 4,303,636
[45] Dec. 1, 1981

[54] CANCER TREATMENT

[76] Inventor: Robert T. Gordon, 4936 W. Estes, Skokie, Ill. 60076

[21] Appl. No.: 905,555

[22] Filed: May 12, 1978

Related U.S. Application Data

[60] Division of Ser. No. 651,395, Jan. 22, 1976, Pat. No. 4,106,488, which is a continuation-in-part of Ser. No. 499,074, Aug. 20, 1974, abandoned.

[51] Int. Cl.³ .................... A61K 43/00; A61K 49/00; G01T 1/00
[52] U.S. Cl. .......................................... 424/1; 128/1.1; 128/653; 128/659; 424/1.5; 424/9
[58] Field of Search ................. 424/1, 1.5, 9; 128/1 R

[56] References Cited

U.S. PATENT DOCUMENTS

| | | | |
|---|---|---|---|
| 3,474,777 | 10/1969 | Figge et al. | 424/1 |
| 3,927,193 | 12/1975 | Hansen et al. | 424/1 |
| 4,065,552 | 12/1977 | Costa | 424/1 |
| 4,106,488 | 8/1978 | Gordon | 424/1 |
| 4,107,283 | 8/1978 | Pratt et al. | 424/1 |
| 4,115,536 | 9/1978 | Rothman et al. | 424/1 |
| 4,115,540 | 9/1978 | Digenis et al. | 424/1.5 |

*Primary Examiner*—Benjamin R. Padgett
*Assistant Examiner*—Christine M. Nucker
*Attorney, Agent, or Firm*—Francis A. Keegan

[57] ABSTRACT

A treatment of cancer by the application of external electromagnetic energy capable of the generation of heat in intracellular particles to induce selective thermal death of cancer cells in living tissue. This process allows for the selective treatment of cancer cells in living tissue without damaging the normal cells by the compartmentalized alteration of biophysical properties in the cancer cell.

7 Claims, No Drawings

CANCER TREATMENT

This is a division of application Ser. No. 651,395, filed Jan. 22, 1976, now U.S. Pat. No. 4,106,488 which is a continuation-in-part application of Ser. No. 499,074 filed Aug. 20, 1974 now abandoned.

The process comprises introducing minute particles into the interior of the cells of living tissue. These particles being injected intravenously while suspended in an appropriate solution are of a size generally having a diameter of approximately 1 micron or less and are of a material with properties, such as ferromagnetic, paramagnetic, or diamagnetic, so as to be inductively heated when subjected to a high frequency alternating electromagnetic field. Introducing the particles as described, the patient is thereafter subjected to an alternating electromagnetic field to inductively heat the particles sufficiently to raise the temperature of the cells by an increment of 8.0°–9.5° Centigrade thus killing the cancer cells without harming the normal cells, since this increment is sufficient to kill the cancer cells but is not great enough to injure the normal cells. Generating the heat intracellularly instead of extracellularly results in the cell's membrane, which is an effective thermal barrier, enhancing the process by keeping the heat within the cells instead of outside of the cells.

The process is further enhanced by the phagocytic characteristic of the cancer cells which causes the particles to concentrate within the cancer cells and thus facilitate a greater generation of heat within the cancer cells. Further selectivity and increased affinity of the cancer cells for these particles may be achieved by incorporating specific radioisotopes or tumor specific antibodies bound to these particles.

These particles introduced intracellularly as described may be used as a method of delivering a chemotherapeutic agent primarily to the interior of the cancer cells by having the chemotherapeutic agent encapsulated within said particles and released at the proper time by application of the high frequency alternating electromagnetic field or by solubilizing the said particles within the cells.

A cancer-treating composition including minute particles suspended in an aqueous solution in dosage form. The said particles may be bound to radioisotopes or to cancer antibodies to more effectively direct the absorption by the cancer cells.

INTRODUCTION

This invention relates generally to a process and composition for the treatment of cancer in living tissues. More particularly, the present invention relates to method and composition for the treatment of cancer by intracellularly killing the cancer cells without injuring the normal cells.

BACKGROUND OF THE INVENTION

There are presently a number of methods and techniques for the treatment of cancer, among which may be included: radiation therapy, chemotherapy, immunotherapy, and surgery. The common characteristic for all of these techniques as well as any other presently known technique is that they are extracellular in scope, that is, the cancer cell is attacked and attempted to be killed through application of the killing force or medium outside of the cell.

This extracellular approach is found to be less effective and efficient because of the difficulties of penetrating the tough outer membrane of the cancer cell that is composed of two protein layers with a lipid layer in between. Of even greater significance is that to overcome the protection afforded the cell by the cell membrane in any extracellular technique, the attack on the cancer cells must be of such intensity that considerable damage is caused to the normal cells resulting in severe side effects upon the patient. Those side effects have been found to limit considerably the effectiveness and usefulness of these treatments.

A safe and effective cancer treatment has been the goal of investigators for a substantial period of time. Such a technique, to be successful in the destruction of the cancer cells, must be selective in effect upon the cancer cells and produce no irreversible damage to the normal cells. In sum, cancer treatment must selectively differentiate cancer cells from normal cells and must selectively weaken or kill the cancer cells without affecting the normal cells.

It has been known that there are certain physical differences that exist between cancer cells and normal cells. One primary physical difference that exists is in the temperature differential characteristics between the cancer cells and the normal cells. Cancer cells, because of their higher rates of metabolism, have higher resting temperatures compared to normal cells. In the living cell, the normal temperature of the cancer cell is known to be 37.5° Centigrade, while that of the normal cell is 37° Centigrade. Another physical characteristic that differentiates the cancer cells from the normal cells is that cancer cells die at lower temperatures than do normal cells. The temperature at which a normal cell will be killed and thereby irreversibly will be unable to perform normal cell functions is a temperature of 46.5° Centigrade, on the average. The cancer cell, in contrast, will be killed at the lower temperature of 45.5° Centigrade. The temperature elevation increment necessary to cause death in the cancer cell is determined to be at least approximately 8.0° Centigrade, while the normal cell can withstand a temperature increase of at least 9.5° Centigrade.

It is known, therefore, that with a given precisely controlled increment of heat, the cancer cells can be selectively destroyed before the death of the normal cells. On the basis of this known differential in temperature characteristics, a number of extracellular attempts have been made to treat cancer by heating the cancer cells in the body. This concept of treatment is referred to as hyperthermia. To achieve these higher temperatures in the cancer cells, researchers have attempted a number of methods including inducing high fevers, utilizing hot baths, diathermy, applying hot wax, and even the implanation of various heating devices in the area of the cancer.

At this time, none of the various approaches to treat cancer have been truly effective and all have the common characteristic of approaching the problem by treating the cancer cell extracellularly. The outer membrane of the cancer cell, being composed of lipids and proteins, is a poor thermal conductor, thus making it difficult for the application of heat by external means to penetrate into the interior of the cell where the intracellular temperature must be raised to effect the death of the cell. If, through the extracellular approaches of the prior hyperthermia techniques, the temperatures were raised so high as to effect an adequate interacellular temperature to kill the cancer cells, many of the normal cells adjacent the application of heat could very well be destroyed.

OBJECT OF THE INVENTION

It is therefore the purpose and principal object of the present invention to kill the cancer cells selectively by intracellularly generating a temperature and by changing biophysical characteristics that will kill the cancer cells while producing no harmful effects upon the normal cells.

DESCRIPTION OF THE INVENTION

The present invention achieves a precise increment of heat rise within the cancer cell and within the cytoplasm. The thermal barrier that characteristically exists as the outer membrane or cell wall of the cell is now utilized as a means of retaining the heat produced within the cell, rather than, as in the past, preventing any heat build-up within the cell. On the basis of the cell resting temperatures and the temperature necessary to produce cell death, the increment that the cell temperature must be raised to cause the cell death is critical. For the normal cell, the temperature rise is 9.5° Centigrade, while in the cancer cell the temperature rise is approximately 8.0° Centigrade. Thus, any temperature rise in the cancer cell or in the normal cell that is at least 8.0° Centigrade and not more than 9.5° Centigrade above the normal cell temperature will result in a selective destruction of the cancer cell without any harmful effects to the normal cell.

In accordance with the present invention, there are found to be a number of approaches that can successfully achieve the end result of an intracellular heat rise and an intracellular destruction of the cancer cell.

In its simplest and broadest aspect, the present invention contemplates the introduction into the cancer cell of a minute particle, such as a ferromagnetic, diamagnetic, or a paramagnetic material, and then subjecting all the cells generally, including the normal cells, to a high-frequency alternating electromagnetic field.

This principle on which the present invention is based is also grounded upon the known fact that cancer cells have a far greater affinity for particles and for foreign substances such as these minute particles that are to be introduced, than do the normal cells. Due to this phagocytic characteristic of cancer cells, such particles tend to concentrate in significantly greater numbers within the cancer cells, as compared to the normal cells. Electronmicrographs have been taken of tissue following the introduction of such particles and clearly illustrate the selective concentration of the particles in the cancer cells. This is expected due to the higher rate of metabolism of the cancer cells and because tumors develop neo-vascularization. The new capillaries and blood vessels formed in tumors have increased permeability to foreign particles when compared to the capillaries and the blood vessels of normal tissues.

The particles which are useful in accordance with the present invention, are those such as the ferromagnetic particles compatible with living tissue may be useful. Similarly, the diamagnetic and paramagnetic materials that may be useful include the following: gallium, indium, technetium, strontium, iodine, and any other diamagnetic and paramagnetic materials compatible with living tissue. The particle size of the particles should be not greater than about 1 micron. Preferable particle size would be less than the 1 micron size.

The minute particles described are to be injected intravenously into the patient through the use of any suitable compatible liquid vehicles. Aqueous solutions of any such body-acceptable materials as dextran, dextrose, saline or blood, as well as water alone, can be used. The liquid vehicle should sustain the particles in suspension for the subsequent injection. Concentrations of such body-acceptable materials that may be useful are those that are up to about 50% by weight in water. Usually a solution of about 1% to 10% is adequate. The concentration of the particles in the solution is not critical and is usually in a range between 50 to 75 mg/cc of the solution.

The intravenous injection into the patient generally is in an amount such that between 1 to 10 mg. of the particles per kg of body weight of the patient are injected at one time; however, up to approximately 20–45 mg. total dosage per kg. of body weight is possible. The greater weight of the patient, the higher the permissible dosage. The total amount of the dosage is not critical though 2 to 3 injections, may be injected within a 24 to 72 hour period. The time span for the injections may vary greatly for various patients and for various objectives.

The minute particles contained in the aqueous medium are transported through the bloodstream and have been found to be phagocytized by the cancerous cells to a far greater degree than, and in fact in some cases to the possible exclusion of, their admittance into the normal cells.

Electronmicrographs of the cancerous tissue have proven the selective pickup of the magnetic particles by the cancer cells.

The intracellular characteristics of the present technique are evident. It has been found that the intracellular temperature of the cells may be raised between 8.0° Centigrade and 9.5° Centigrade to cause death in the cancer cell without damage being caused to the normal cells.

The next stage of the present invention is to bring about by inductive heating with high-frequency alternating electromagnetic field a precise rise in the temperature of the cell. The principle of inductive heating through the use of hysteresis is a known principle. Similarly, the monitoring of the temperatures of the living cells is a presently available technique well-known to the medical science.

The inductive heating of the minute particles is achieved by using an electronic oscillator operating in the high-frequency range which heats the particles by subjecting them to an intense high-frequency field within a large but otherwise conventional helical coil, field energy being converted to heat through hysteresis losses and the resistive dissipation of eddy currents. The helical inductive coil is of sufficient internal diameter to permit the patient to pass within and of such length to encompass the length of the patient. Generally, the internal diameter should be at least 2 feet, but preferably would be greater than 3–6 feet in diameter. No maximum diameter is known to exist except that required from practical and economical considerations. Diameters of inductive coils of greater than 6 feet have a preferential effect in the overall process by providing a more uniform flux gradient to the patient.

The frequency of the electromagnetic alternating high frequency field will range from 50 kilohertz to 10 megahertz and the power input of the oscillator-generator will range from 0.5 kilowatts to 1.0 kilowatts per kg. of patient body weight 0.75 kilowatts of power per 1.0 kilograms of body weight has been found to be particularly useful. In this power and frequency range, the coil is selected to produce from 400 to 800 oersteds, preferably 550–650 oersteds.

The time necessary to inductively heat the minute particles held within the cells to be treated depends substantially upon the frequency and the power producing the alternating electromagnetic field and ultimately the strength of the field produced. In general, it has been found that subjecting the patient to 5 to 12 minutes or preferably 8 to 10 minutes of the alternating electromagnetic field would be adequate to bring about the necessary temperature rise of at least 8.0° Centigrade. It should be clearly understood that it is only necessary to raise the temperature of the cancer cell above 8.0° Centigrade and that the variables with respect to the type and concentration of the particles in the vehicle and the electromagnetic treatment are not critical provided that the necessary temperature is achieved.

EXAMPLE I

As a specific example of the simplest form of the present invention, ferric hydroxide particles of 0.7 micron size are suspended in a 5% dextrose aqueous solution in an amount of about 50 mg of the particles per cc. Dosages in the amount of 30 mg. per kg. of body weight each of the particles should be made twice, by intravenous injections, each being 24 hours apart. The patient is then ready for the electromagnetic treatment by insertion entirely within an inductive coil 3 feet in diameter. The coil is connected to an alternating current generator, producing a frequency of 3 megahertz and a field of 600 oersteds. The patient is to be subjected to the electromagnetic treatments about 12 hours after the last injection. The inductive heating of the particles within the cancer cells is between 8 and 10 minutes, during which time the temperature within the cell will have been increased 8.5° Centigrade. At this temperature, the cancerous cells in the living tissue will have been killed while the normal cells will recover normal cellular functions.

While the simplest aspect of the invention has been described in detail, the selectivity of the magnetic particles for the cancer cells may be increased through the use of several techniques.

The addition of a cancer cell seeking agent such as radioisotopes or a tumor specific antibody is useful in directing the minute particles more selectively to the cancer cells. It is known that both radioisotopes and tumor specific antibodies have an affinity for the cancer cells and it is for this reason that the radioisotopes and antibodies have been found to have some application in the treatment of certain tumors. It is also possible that the radioisotopes may be used to substitute for the magnetic particles and be injected intravenously so as to be selectively taken up by the cancerous cells. Many of these radioisotopes are inherently paramagnetic or diamagnetic and whether chemically or physically combined with other particles or used alone, the effect of the alternating electromagnetic field upon the magnetic particles and/or the radioisotopes would be to raise the temperature of the cancerous cell to the destructive temperature. Typical examples of useful radioisotopes are such as gallium-67, indium-113m, technetium-99m, fluorine, selenium-75. A great many other radioisotopes are useful and the above are only examples. The size and concentration of the radioisotopes alone or attached to the minute particles and the manner of injection is precisely the same as previously described.

These radioisotopes or antibodies may be bound to the particles as iodine-131 (the ratioisotope) has been bound to albumin for lung scanning in the past. Antibodies, for instance, may be attached to the ferromagnetic, paramagnetic, or diamagnetic particles by use of an intermediate reducing glucose unit or its derivative such as metasaccharinic acid, in a conventional manner and as described in Example III, much as high molecular weight dextran is bound to ferric hydroxide.

It is known that antibodies can be formed by injection of cancer cells removed from one patient with cancer and injected into another patient. The injection of the cancer cells will in turn form antibodies in the substitute host as a defense against the foreign tumor cells from the original donor. These antibodies can be then selectively isolated and in the past have been used to treat selected specific tumors. These antibodies have usefulness, in the present invention as a selective cancer cell seeking agent.

These antibodies may be bound chemically or physically to the minute particles and then re-injected into the patient to be treated. Due to the antibodies' specificity for the original tumor cells, the antibodies bound to the particles will even more selectively induce the particles to be phagocytized by the cancer cells.

Antibodies with radioactive isotopes may be produced by feeding the animals producing the antibodies, labeled amino acids. This labeled amino acid is then incorporated into the antibody.

Large chemical entities can be attached to antibody molecules. Large proteins may be attached via diagotized atoxyl (p-amino-benzene arsenic acid). Antibodies may be bound while they are attached to a hapten or to an antigen. This protects the immunologically specific site of the antibody during the binding procedure.

It should be understood that the entire purpose of selective direction of the particles or the radioisotopes is that the presence of an alternating electromagnetic field will produce heat intracellularly to raise the temperature of the cell between the 8.0° Centigrade and the 9.5° Centigrade range. Thus, even if all of the cells were to possess an equal concentration of the particles, the application of the induction heating would produce a similar rise in temperature in all cells, which within the range desired, would do no harm to the normal cells while killing the cancer cells. There does not appear to be any danger in an increased concentration of the particles in the normal cells in view of the phagocytic characteristics of the cancer cells, but to efficiently use all of the magnetic particles and to permit the smallest dosage possible, it is desirable to utilize where beneficial a selective cancer cell seeking agent such as the radioisotopes or the antibodies. In this manner, an even greater concentration of the magnetic particles should be found in the cancer cells and a very minor amount if not an exclusion of such particles in the normal cells.

A specific example of the use of a radioisotope in accordance with the present invention is as follows:

EXAMPLE II

Gallium citrate-gallium-67 is incorporated into a sterilized isotonic 5% saline solution, the concentration being 1 millicurie of gallium-67 per cc of the total composition. The amount to be injected could vary between 0.02 millicuries up to 0.1 millicuries per kg. of body weight. Upon injection, a 12-hour period is allotted for the gallium to isolate itself and selectively concentrate within the cancerous cells. Thereafter, the same alternating electromagnetic field is applied in exactly the same manner as previously described in Example I. The amount of intracellular temperature increase is above 8.0° Centigrade and below 9.5° Centigrade and produces selective killing of the cancer cells without harming the normal cells.

When the gallium-67 is to be utilized as a cancer cell seeking agent, it may be bound to the particle in accordance with the manner in which iodine-131 has been bound to albumin. This combined gallium particle may be injected into the patient in precisely the same manner and it would be found that the gallium selectively delivers the particles to the cancer cells. Thereafter, when the cancer cell is subjected to the alternating electromagnetic field, the intracellular temperature of the cancer cell is raised above the critical increase of 8.0° Centigrade to selectively destroy the cancer cell.

It is also possible that the known utility of the tumor specific cancer agents such as the chemotherapeutic agents, the radioisotopes or tumor specific cancer antibodies may be utilized in accordance with the present invention. For example, chemotherapeutic agents include 5-flurouracil, nitrogen mustard, actinomycin D, methotrexate, cytoxon and vincristine amongst a number of other agents known for similar utility. It is an aspect of the present invention that such known chemotherapeutic agents in a size less than 1 micron may be coated with ferromagnetic material to produce a total particle of a size less than the approximate 1 micron particle size. The particles in effect encapsulate the chemotherapeutic agent and form a micro-sphere around the chemotherapeutic agent. The coating thickness of the magnetic particle should be approximately 0.1 micron. Thus, the size of the chemotherapeutic agent particle should be about 0.1 micron or less in order to to bring about the total particle size of not greater than 1 micron and preferably less.

EXAMPLE III

The following is an example of the method of coating 5-flurouracil with a ferromagnetic material: 5-flurouracil, a known acknowledged effective chemotherapeutic agent against cancer, is taken in its solid state and pulverized into particles 0.5 micron in size. These particles, in turn, are then coated with ferric hydroxide approximately 0.1 micron in thickness, in accordance with any of the conventional methods of coating submicron particles as described in U.S. Pat. No. 3,294,686.

These particles are then colloidally suspended in a 6% by weight aqueous dextran solution. This solution is introduced intravenously to the patient with the result that due to the phagocytic characteristics of the cancer cells, most of these particles will be deposited in the cytoplasm inside the cancer cells. This would take place about 4 to 8 hours after the intravenous injection. After the particles' deposition into the cytoplasm, the ferric hydroxide is acted upon by the cytoplasm and is converted to an organic iron complex (ferritin) which is then absorbed.

After approximately 24 hours, the ferric hydroxide coating is thus solubilized and the chemotherapeutic agent 5-flurouracil is released within the cancer cell where it can effectively kill the cell. Time is not critical, and may vary from 1 to 48 hours or more. The other tumor specific cancer agents may be similarly utilized.

EXAMPLE IV

The chemotherapeutic agent as encapsulated in a ferromagnetic material, as described in Example III, may be injected in precisely the same manner and alternatively subjected to the high frequency alternating electromagnetic field of Example I which then is capable of breaking up the micro-sphere of the magnetic material by a vibrational frequency produced by the electromagnetic field at which the outer surface resonates and its integrity is destroyed. Upon breakup of the micro-spheres the chemotherapeutic agent is released intracellularly and selectively within the cancer cells. The same example may be applied in the same manner to the other tumor specific cancer agents.

EXAMPLE V

The encapsulating material may also contain a low melting solid such as wax having a melting point higher than the temperature of the cells but below the death temperature of the normal cell. This temperature range may be therefore between about 37° and 46.5° Centigrade. This wax is in combination with the ferromagnetic material and applied as in Example III. In this alterhative embodiment the application of the alternating electromagnetic field, as in Example I, would melt the low melting solid due to the induction heating of the ferromagnetic material and release the chemotherapeutic agent within the cancer cells. Similarly, the other tumor specific cancer agents may be similarly utilized.

As previously stated, a cancer cell seeking agent such as the radioisotope or antibodies may be utilized to more selectively direct the micro-sphere containing the chemotherapeutic agent to the particular cancer cell. As is known, chemotherapeutic agents sometimes have adverse side effects upon normal cells, but the present procedure would selectively release the chemotherapeutic agent intracellularly and selectively. Compared to the presence of the chemotherapeutic agent in the cancerous cell, the concentration of the chemotherapeutic agent in the normal cell would be minimal. The undesirable side effects upon the normal cells should therefore be greatly minimized if not totally avoided.

A further embodiment of the present invention which typifies the broad nature of the invention is the incoporation of any tumor specific cancer antibody or cancer treating radioisotope within the encapsulating ferromagnetic micro-sphere in the manner previously described in Example III. Thereafter the antibody or radioactive isotope so coated may be introduced within the cell walls of the cancer cell and the alternating electromagnetic field applied as in Example IV to cause the micro-spheres of the ferromagnetic material to release the antibody or the radioisotope intracellularly. It is also possible that the release of the encapsulated material may be by solubilizing the spheres within the cell, as previously described in Example III.

One of the important features of the present invention is that there is destruction of the cancerous cells wherever they are located in the patient. Cells that may have become detached from the tumor and drift in the vascular system or lymphatic system would be killed by the present process.

There are many variations of the invention as described and this invention should be limited solely by the scope of the following claims.

I claim:

1. A cancer treating composition for intravenous injection comprising: inductively heatable particles selected from the group consisting of ferromagnetic, paramagnetic and diamagnetic and of not greater than 1 micron suspended in an aqueous solution in dosage form.

2. The composition of claim 1 wherein the aqueous solution is a solution of dextrose, dextran, saline, or blood and wherein the aqueous solution is at a 1% to 10% solution.

3. The composition of claim 1 including a cancer cell seeking agent excluding said particles and selected from radioisotopes and antibodies specific for treating cancer.

4. The composition of claim 1 including said particles coating a chemotherapeutic agent for the treatment of cancer.

5. The composition of claim 4 wherein said particles encapsulate the chemotherapeutic agent with a coating not greater than 0.1 micron.

6. The composition of claim 5 wherein the particle encapsulated therapeutic agent has a diameter not greater than approximately 1 micron.

7. The composition of claim 5 including a cancer cell seeking agent excluding said particles being bound to said particles.

* * * * *